(12) United States Patent
Hull

(10) Patent No.: US 9,427,153 B1
(45) Date of Patent: Aug. 30, 2016

(54) CORNEAL COVER AND METHOD OF USE THEREOF

(71) Applicant: Thomas P. Hull, Akron, OH (US)

(72) Inventor: Thomas P. Hull, Akron, OH (US)

( * ) Notice: Subject to any disclaimer, the term of this patent is extended or adjusted under 35 U.S.C. 154(b) by 0 days.

(21) Appl. No.: 14/723,702

(22) Filed: May 28, 2015

Related U.S. Application Data

(60) Provisional application No. 62/131,348, filed on Mar. 11, 2015.

(51) Int. Cl.
| A61F 9/00 | (2006.01) |
| A61B 3/107 | (2006.01) |
| A61B 3/10 | (2006.01) |
| A61B 3/117 | (2006.01) |
| A61F 9/007 | (2006.01) |

(52) U.S. Cl.
CPC .............. *A61B 3/107* (2013.01); *A61B 3/10* (2013.01); *A61B 3/117* (2013.01); *A61F 9/00736* (2013.01)

(58) Field of Classification Search
CPC .......... A61F 2/14; A61F 2/142; A61F 2/145; A61F 9/04; A61F 9/0017
See application file for complete search history.

(56) References Cited

U.S. PATENT DOCUMENTS

| 1,921,972 A | 8/1933 | Fertsch et al. |
| 2,129,304 A | 9/1938 | Feinbloom |
| 2,129,305 A | 9/1938 | Feinbloom |
| 2,178,873 A | 11/1939 | Feinbloom |
| 2,196,066 A | 4/1940 | Feinbloom |
| 2,330,837 A | 10/1943 | Mullen |
| 2,438,743 A | 3/1948 | Feinbloom |
| 2,510,438 A | 6/1950 | Tuohy |
| 3,102,157 A * | 8/1963 | Gamber .................. G02C 7/04 351/159.05 |
| 3,228,741 A | 1/1966 | Becker |
| 3,482,906 A | 12/1969 | Volk |
| 3,781,096 A | 12/1973 | Townsley |
| 3,937,566 A | 2/1976 | Townsley |
| RE29,229 E | 5/1977 | Girard et al. |
| 4,194,815 A | 3/1980 | Trombley |
| 4,198,131 A | 4/1980 | Birdsall et al. |
| 4,469,646 A * | 9/1984 | Rawlings ............ B29C 33/0038 264/1.1 |
| 4,570,626 A * | 2/1986 | Norris .................... A61B 19/40 128/858 |
| 4,582,404 A * | 4/1986 | Hamilton ............... A61B 3/107 351/212 |
| 5,487,394 A * | 1/1996 | Shiu ...................... A61F 9/0017 128/846 |
| 6,123,081 A * | 9/2000 | Durette ................ A61F 9/0017 128/858 |
| 7,699,465 B2 * | 4/2010 | Dootjes .................... G02C 7/04 351/159.73 |
| 8,857,438 B2 * | 10/2014 | Barthe ...................... A61N 7/00 128/846 |
| 2003/0060692 A1* | 3/2003 | Ruchti ................. A61B 5/0064 600/310 |
| 2012/0245683 A1* | 9/2012 | Christie .................. A61F 2/145 623/5.11 |
| 2014/0371565 A1* | 12/2014 | Glasser ............. A61N 1/36046 600/383 |

FOREIGN PATENT DOCUMENTS

CA 663765 5/1963

* cited by examiner

Primary Examiner — Ashley Fishback
(74) Attorney, Agent, or Firm — Martin & Ferraro, LLP

(57) ABSTRACT

A corneal cover for placement on a patient's eye during eye surgery. A generally concave central arcuate portion has a first radius of curvature. A generally concave peripheral arcuate portion has a second radius of curvature larger than the first radius of curvature. One of a stem projecting from the peripheral arcuate portion, and a lip projecting from an outer periphery is provided to grasp the corneal cover, with a tool or manually, to place it on the eye and to remove it from the eye. The corneal cover has substantially no corrective power. The corneal cover is made of a hydrophobic material so it does not need to be irrigated during surgery.

29 Claims, 2 Drawing Sheets

US 9,427,153 B1

CORNEAL COVER AND METHOD OF USE THEREOF

The present application claims the benefit of U.S. Provisional Application No. 62/131,348, filed Mar. 11, 2015, which is incorporated by reference herein.

FIELD OF THE INVENTION

The present invention relates to a corneal cover, and a method of performing surgery on a surgical site in a patient's eye, using the corneal cover.

DESCRIPTION OF THE RELATED ART

It is known to use a wide-field non-contact viewing instrument during surgery, e.g., a vitrectomy, on a surgical site in a patient's eye. The surgeon uses the wide-field non-contact viewing system to view the surgical site through the patient's cornea. The clarity of the view, however, is dependent on keeping the patient's cornea well hydrated. Difficulty is encountered trying to irrigate the cornea during vitrectomy surgery due to the close proximity of the viewing instrument lens and the corneal surface. The surgery is frequently interrupted to allow the surgeon's assistant to re-wet the cornea. In some cases, irrigation liquid splashes onto the viewing instrument lens, creating water spots, which must be dried off, further interrupting the surgery.

Another disadvantage with the related art occurs during long, involved eye surgeries. During such long, involved surgeries, the surface of the patient's cornea can deteriorate. Such deterioration requires removal of the outer layer of the cornea, i.e., the corneal epithelium, by scraping it with an appropriate surgical tool. After the corneal epithelium is removed, near—constant corneal irrigation is required, and the patient experiences significant post—operative discomfort.

SUMMARY OF THE INVENTION

It is an object of one embodiment of the present invention to provide a corneal cover, and a method of use thereof, which will enable a surgeon to view a surgical site in a patient's eye during surgery on the eye, without having to interrupt the surgery to irrigate the cornea or to clear the viewing instrument lens of inadvertent irrigation liquid drops.

It is another object of one embodiment of the present invention to provide a corneal cover, and a method of use thereof, wherein the lens of the corneal cover has nearly constant clarity.

It is a further object of one embodiment of the present invention to provide a corneal cover, and method of use thereof, which compensate for an astigmatism present in the patient's cornea.

It is a further object of one embodiment of the present invention to provide a corneal cover, and a method of use thereof, which reduces the likelihood for the need, during long, involved eye surgeries, to scrape corroded tissue off of the patient's corneal epithelium, thereby reducing post-operative discomfort.

These and other objects of the present invention will be apparent from review of the following specification and the accompanying drawings.

In view of the above objectives of the invention, a corneal cover for placement on an eye of a patient during eye surgery, the corneal cover as depicted, disclosed, and claimed below, substantially obviates one or more of the disadvantages of the related art.

In one preferred embodiment of the corneal cover in accordance with the invention, the corneal cover includes a central arcuate portion having a first radius of curvature, a generally concave lower surface and a generally convex upper surface, the generally concave lower surface being adapted to cover a cornea of a patient's eye, a peripheral arcuate portion having a second radius of curvature, the peripheral arcuate portion having a generally concave lower surface and a generally convex upper surface, the generally concave lower surface being adapted to cover at least a portion of a sclera of the patient's eye, and one of a stem projecting from a selected position on the peripheral arcuate portion and a lip projecting from at least a portion of an outer periphery of the peripheral arcuate portion, the corneal cover being made of a hydrophobic material.

The first radius of curvature preferably is between approximately 7 mm and approximately 8.5 mm, more preferably between approximately 7.5 mm and approximately 8.0 mm, and even more preferably between approximately 7.7 mm and approximately 7.9 mm.

The second radius of curvature preferably is between approximately 11 mm and approximately 13 mm, more preferably between approximately 11.5 mm and approximately 12.5 mm, and even more preferably approximately 12 mm.

The hydrophobic material preferably includes a hard plastic.

The central arcuate portion preferably has a thickness between the lower surface and the upper surface of between approximately 0.5 mm and 2.0 mm, and more preferably between approximately 0.5 mm and approximately 1.0 mm.

A diameter of the corneal cover, measured across the outer periphery of the peripheral arcuate portion, preferably is between approximately 12 mm and approximately 18 mm, and more preferably between approximately 13 mm and 16 mm.

The one of the stem and the lip of the one preferred embodiment of the corneal cover in accordance with the invention preferably has a length of less than or equal to approximately ⅓ of the diameter, preferably between approximately 1 mm and approximately 5 mm, and more preferably between approximately 2 mm and approximately 3 mm.

The generally concave lower surface of the central arcuate portion preferably conforms to a generally convex surface of the cornea of the patient's eye.

The general concave lower surface of the peripheral arcuate portion preferably corresponds to a generally convex surface of the at least the portion of the sclera of the patient's eye.

The corneal cover preferably has a corrective power between approximately −4 diopters and approximately +4 diopters, and more preferably approximately 0 diopters.

In one preferred embodiment of a method of performing a surgery on a surgical site in a patient's eye in accordance with one embodiment of the invention, the method includes utilizing a corneal cover, the corneal cover including a central arcuate portion having a first radius of curvature, the first radius of curvature being between approximately 7 mm and approximately 8.5 mm, the central arcuate portion having a generally concave lower surface and a generally convex upper surface, the generally concave lower surface being adapted to cover a cornea of the patient's eye, a peripheral arcuate portion having a second radius of curvature, the second radius of curvature being approximately 11 mm and approximately 13 mm, the peripheral arcuate portion having a generally concave lower surface and a generally convex upper surface, the generally concave lower surface being adapted to cover at least a portion of a sclera of the patient's eye, and one of a stem projecting from a selected position on the peripheral arcuate portion and a lip projecting from at least a portion of an outer periphery of the peripheral arcuate portion, wherein the corneal cover has a corrective power of substantially 0 diopters, and wherein the corneal cover is made of a hydrophobic material, preparing the patient's eye for the surgery, making at least one incision in a portion of the patient's sclera, installing the corneal cover on the patient's eye such that the peripheral arcuate portion of the corneal cover does not cover the at least one incision; inserting at least one surgical instrument into the at least one incision, observing the surgical site through the central arcuate portion, and performing the surgery with the at least one surgical tool.

Performing the surgery with the at least one surgical tool preferably includes performing a vitrectomy.

Installing the corneal cover on the patient's eye preferably includes placing the corneal cover on the patient's eye with a viscoelastic material being on at least one of the corneal cover and the eye prior to placing the corneal cover onto the eye, an interface between the corneal cover and the viscoelastic material defining a tear film, the tear film providing a correction for an astigmatism present in the patient's eye.

DETAILED DESCRIPTION OF THE PREFERRED EMBODIMENT

Figure 1:
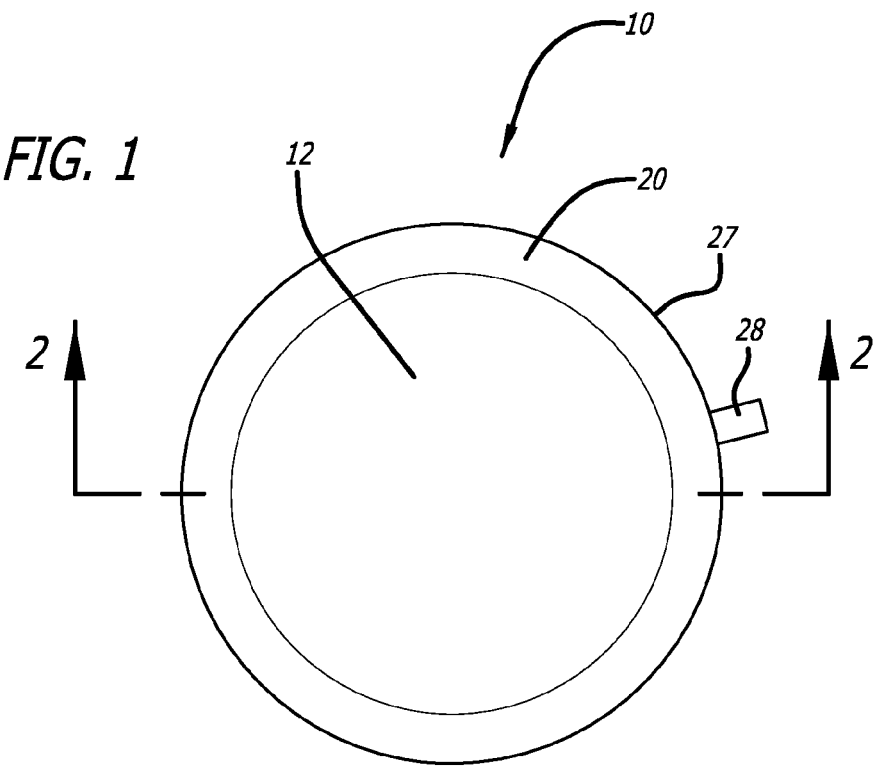
FIG. 1 is an upper plan view of a corneal cover in accordance with one embodiment of the invention.
Figure 2:
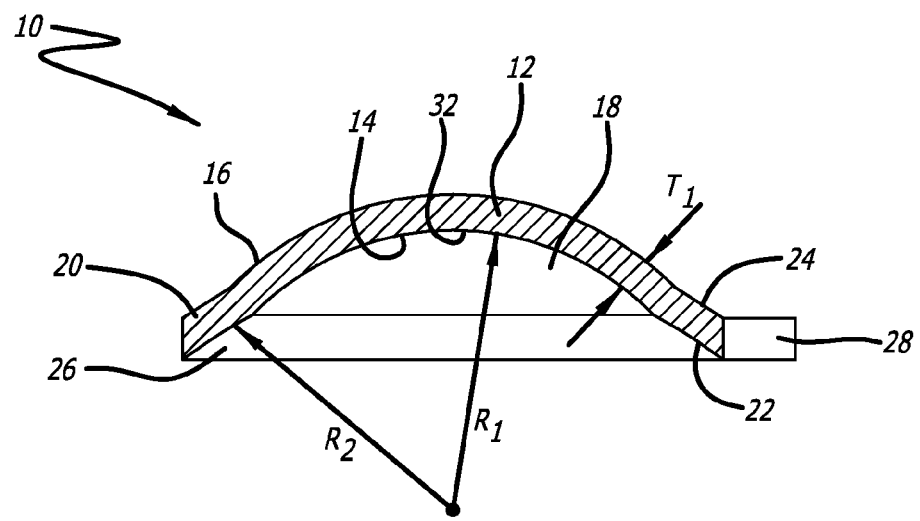
FIG. 2 is a side cross-sectional view of the corneal cover, viewed along line 2 of FIG. 1.

Other embodiments of the invention will be apparent to those skilled in the art from consideration of the specification and practice of the invention disclosed herein. It is intended that the specification be considered as exemplary only, with a true scope and spirit of the invention being indicated by the following claims.

In one preferred embodiment of the invention, as depicted in FIGS. 1-4B, a corneal cover 10 includes a central arcuate portion 12. The central arcuate portion 12 includes a concave lower surface 14 and a convex upper surface 16. The concave lower surface 14 is configured to cover a cornea 18 of a patient's eye, conforming substantially to a convex surface of the cornea 18. The central arcuate portion 12 preferably has a thickness T1 between the concave lower surface 14 and the convex upper surface 16 of preferably between approximately 0.5 mm and approximately 2.0 mm, and more preferably between approximately 0.5 mm and 1.0 mm. The central arcuate portion further has a first radius of curvature R1 of preferably between approximately 7 mm and approximately 8.5 mm, and more preferably between approximately 7.5 mm and approximately 8 mm, and even more preferably between about 7.7 mm and 7.9 mm.

In one preferred embodiment of the invention, as depicted in FIGS. 1-4B, the corneal cover 10 further includes a peripheral arcuate portion 20. The peripheral arcuate portion 20 includes a concave lower surface 22 and a convex upper surface 24. The concave lower surface 22 is configured to cover a portion of a sclera 26 of the patient's eye. In the embodiment of the invention shown in FIGS. 1 and 2, the peripheral arcuate portion 20 has a second arc of curvature R2 which is greater than the first arc of curvature R1, of preferably between approximately 11 mm and approximately 13 mm, more preferably between approximately 11.5 mm and approximately 12.5 mm, and even more preferably approximately 12 mm.

In one preferred embodiment of the invention, the corneal cover 10 is made of a gas impermeable hydrophobic material, preferably hard plastic. In one preferred embodiment, the hydrophobic hard plastic further includes a hard acrylic, e.g., PMMA. The corneal cover 10 preferably is made of a hydrophobic material so it will not need to be irrigated during surgery.

In one preferred embodiment of the invention, the corneal cover 10 has no corrective power, e.g., approximately 0 diopters. It is within the scope of the invention, however, for the corneal cover 10 to include some mild corrective power, e.g., approximately +4 diopters to −4 diopters.

Figure 3A:
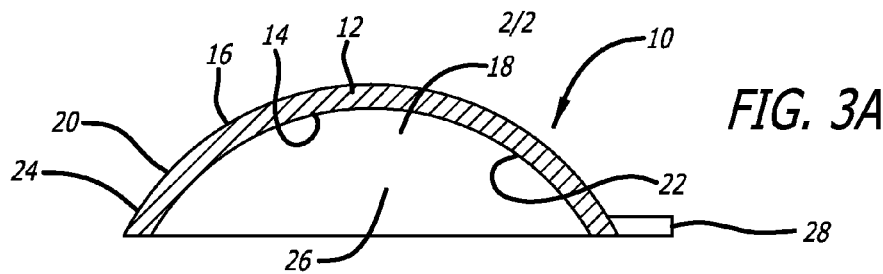
FIG. 3A is a side plan view of a corneal cover having a single concave radius in accordance with another embodiment of the invention, depicting a stem configured to place the corneal cover on the patient's eye, and remove the corneal cover from a patient's eye.
Figure 3B:
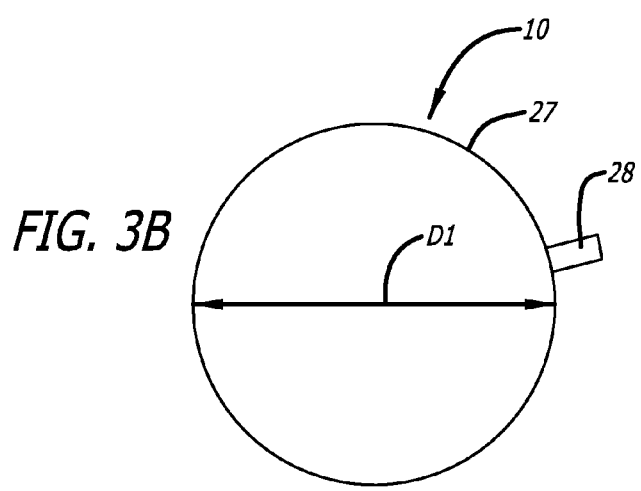
FIG. 3B is an upper plan view of the embodiment of FIG. 3A.

In one preferred embodiment of the invention, as depicted in FIGS. 3A-3B, the corneal cover 10 has a diameter D1, measured across an outer periphery 27 of the peripheral arcuate portion 20. Diameter D1 is preferably between approximately 13 mm and approximately 18 mm.

In one preferred embodiment of the invention, and as embodied in FIGS. 1-3B, corneal cover 10 includes a stem 28 projecting from a position on the peripheral arcuate portion 20. The stem 28 is configured to be grasped, either by a surgical tool, or manually by a hand of a surgeon to both place the corneal cover 10 on the patient's eye, and remove the corneal cover 10 from the patient's eye. The stem 28 preferably has a length no greater than ⅓ of the diameter D1, in order to provide a grasping surface without interfering with the work of the surgeon, The length of the stem 28 is preferably between approximately 1 mm and approximately 5 mm, and more preferably between approximately 2 mm and approximately 3 mm. The stem 28 preferably is made of the same hydrophobic material as the corneal cover 10, and preferably is attached to the corneal cover 10 as part of a unitary device. As depicted in FIGS. 1-3B, the stem 28 projects from the outer periphery 27 of the peripheral arcuate portion 20. It is within the scope of the invention, however, for the stem 28 to project from any selected position on the peripheral arcuate portion 20.

Figure 4A:
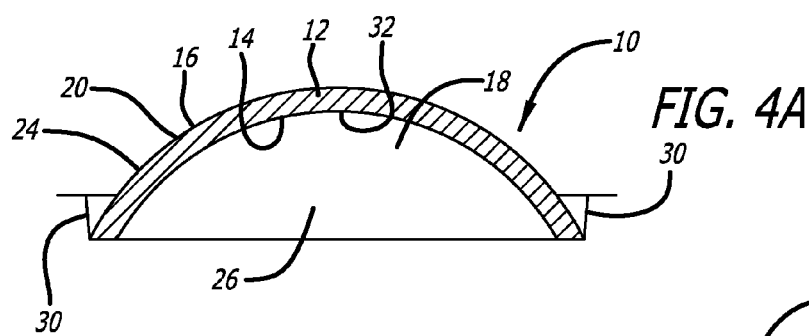
FIG. 4A is a side plan view of a corneal cover in accordance with yet another embodiment of the invention, depicting a lip configured to place the corneal cover on the patient's eye, and remove the corneal cover from the patient's eye.
Figure 4B:
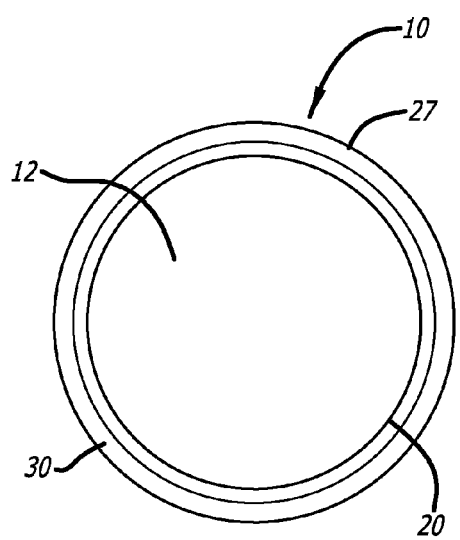
FIG. 4B is an upper plan view of the embodiment of FIG. 4A.

In one preferred embodiment, and as embodied in FIGS. 4A-4B, an additional, or alternate, grasping device can be provided with the corneal cover 10. A lip 30 projects from the outer periphery 27 of the outer peripheral portion 20. The lip 30 can project from the entire 360° of the outer periphery 27, or only a portion thereof. The lip 30, like the stem 28 is configured, and has a selected length, allowing it to be grasped by either a surgical tool or the hand of the surgeon, in order to place the corneal cover 10 on the eye of the patient, or remove the corneal cover from the eye of the patient, without being so large as to interfere with the surgery. The stem 28 and the lip 30 can be used either separately or together to facilitate placement of the corneal cover 10 on the patient's eye, or remove the corneal cover 10 from the patient's eye.

Although certain preferred embodiments of the present invention include the peripheral arcuate portion 20 having a second arc of curvature R2 which is greater than the first arc of curvature R1, in other preferred embodiments that include at least one of stem 28 and lip 30 or some other projection used to facilitate placement of the corneal cover onto the eye and removal therefrom during surgery, R1 and R2 can be the same.

The preferred embodiment of the present invention, as described and depicted above, is used to perform surgery, e.g., a vitrectomy, on a surgical site in a patient's eye.

Initially, the patient's eye is prepared for surgery using known techniques and procedures, e.g., administering at least a local anesthetic, and using conventional surgical clamps to clamp the patient's eyelids open far enough to leave the patient's cornea and sclera unobstructed.

The surgeon, or the surgeon's assistant, places the corneal cover 10 on the patient's eye with a viscoelastic material, e.g., GONIOSOL®. An interface between the corneal cover 10 and the viscoelastic material defines a tear film 32, which functions to compensate for any astigmatism present in the patient's eye. Placement of the corneal cover 10 on the patient's eye can include grasping one or both of the stem 28 and the lip 30, either manually or with a tool, and placing the corneal cover 10 in the desired location on the eye, with the central arcuate portion 12 covering the patient's cornea 18, and the peripheral arcuate portion 20 covering a portion of the patient's sclera 26.

The surgeon makes at least one incision (not shown) at a selected position in the sclera 26, and inserts at least one surgical tool (not shown) through the at least one incision. It is within the scope of the invention for the steps of making the incision, and inserting the surgical tool therethrough, to be performed either before or after placing the corneal cover 10 on the patient's eye.

While performing the surgery, the surgeon can view the surgical site in the patient's eye by looking through a viewing instrument, e.g., a microscope (not shown) positioned over the central arcuate portion 12 and the patient's cornea 18. The surgery proceeds without interruption caused by a need to irrigate the corneal cover 10, or by a need to clean inadvertent irrigation liquid spots off the viewing instrument lens. The clarity of the image is clear and constant, without "waves" of clarity that typically accompany periodic corneal irrigation. In some cases, the role of the surgical assistant can be limited to handing needed surgical tools to the surgeon; in other cases, e.g., where state laws allow, it is envisioned that the need for a surgical assistant potentially may be eliminated.

A significant advantage of the corneal cover 10, as described and depicted above, exists in long, involved eye surgeries. With use of the corneal cover 10, even in the case of long, involved eye surgeries, the cornea 18 looks pristine. Scraping of the corneal epithelium, therefore, is avoided, substantially reducing post-operative discomfort experience by the patient.

After the surgery is complete, the surgeon removes the corneal cover 10. Removal can be performed utilizing the one of the stem 26 and the lip 30. The corneal cover 10 may be made as a disposable, single-use product, to avoid cost and time associated with cleaning and disinfecting it between surgeries.

I claim:

1. A corneal cover for placement on an eye of a patient during eye surgery, the corneal cover comprising:
   a central arcuate portion having a first radius of curvature, the first radius of curvature being between approximately 7 mm and approximately 8.5 mm, the central arcuate portion having a generally concave lower surface and a generally convex upper surface, the generally concave lower surface being adapted to substantially conform to a generally convex upper surface of a cornea of the patient's eye, and to substantially cover the cornea of the patient's eye;
   a peripheral arcuate portion having a second radius of curvature, the second radius of curvature being between approximately 11 mm and approximately 13 mm, the peripheral arcuate portion having a generally concave lower surface, a generally convex upper surface, and an outer periphery, the generally concave lower surface being adapted to substantially conform to a generally convex upper surface of at least a portion of a sclera of the patient's eye, and to substantially cover the at least the portion of the sclera of the patient's eye; and
   a lip projecting from at least a portion of the outer periphery of the peripheral arcuate portion;
   wherein the corneal cover is configured without a corrective power to correct vision of the patient; and
   wherein the corneal cover is made of a hydrophobic material.

2. The corneal cover as recited in claim 1, wherein the hydrophopic material includes a hard plastic.

3. The corneal cover as recited in claim 1, wherein the central arcuate portion has a thickness between the lower surface and the upper surface of between approximately 0.5 mm and approximately 2.0 mm.

4. The corneal cover as recited in claim 3, wherein the thickness is between approximately 0.5 mm and approximately 1.0 mm.

5. The corneal cover as recited in claim 1, wherein the lip has a length of between approximately 1 mm and approximately 5 mm.

6. The corneal cover as recited in claim 5, wherein the lip has a length of between approximately 2 mm and approximately 3 mm.

7. The corneal cover as recited in claim 1, wherein the lip is configured to be grasped by one of a tool and a hand.

8. The corneal cover as recited in claim 1, wherein the first radius of curvature is between approximately 7.5 mm and 8.0 mm.

9. The corneal cover as recited in claim 1, wherein the first radius of curvature is between approximately 7.7 mm and approximately 7.9 mm.

10. The corneal cover as recited in claim 1, having a diameter measured across the outer periphery of the peripheral arcuate portion of between approximately 13 mm and approximately 18 mm.

11. The corneal cover as recited in claim 10, wherein the diameter is between approximately 15 mm and approximately 16 mm.

12. The corneal cover as recited in claim 1, wherein the lip has a length of one of less than and equal to approximately 1/3 of a diameter of the corneal cover.

13. A corneal cover as recited in claim 1, wherein the corneal cover is further configured for placement on the patient's eye with a viscoelastic material.

14. A corneal cover for placement on an eye of a patient during eye surgery, the corneal cover comprising:

a central arcuate portion having a first radius of curvature, the central arcuate portion having a generally concave lower surface and a generally convex upper surface, the generally concave lower surface being adapted to substantially conform to a generally convex outer surface of a cornea of the patient's eye, and to substantially cover the cornea of the patient's eye;

a peripheral arcuate portion having a second radius of curvature, the second radius of curvature being greater than the first radius of curvature, the peripheral arcuate portion being configured to substantially cover at least a portion of a sclera of the patient's eye, and having at least a generally concave lower surface and a generally convex upper surface, the generally concave lower surface being adapted to substantially conform to a generally convex outer surface of the at least the portion of hall the sclera of the patients eye; and a stem projecting from an outer periphery of the peripheral arcuate portion, the stem being configured to be grasped by one of a hand and a tool, for one of placement on and removal from the patient's eye;

wherein the corneal cover has a corrective power of between approximately −4 diopters and +4 diopters; and wherein the corneal cover is made of a gas impermeable hydrophobic material.

15. The corneal cover as recited in claim 14, wherein the first radius of curvature is between approximately 7 mm and approximately 8.5 mm.

16. The corneal cover as recited in claim 14, wherein the second radius of curvature is between approximately 11 mm and approximately 13 mm.

17. The corneal cover as recited in claim 14, wherein the corrective power is approximately 0 diopters.

18. A method of performing a surgery on a surgical site in a patient's eye, the method comprising:

utilizing a corneal cover, the corneal cover including:
a central arcuate portion having a first radius of curvature, the first radius of curvature being between approximately 7 mm and approximately 8.5 mm, the central arcuate portion having a generally concave lower surface and a generally convex upper surface, the generally concave lower surface being adapted to substantially conform to a generally convex outer surface of a cornea of the patient's eye, and to substantially cover the cornea of the patient's eye;

a peripheral arcuate portion having a second radius of curvature, the second radius of curvature being between approximately 11 mm and approximately 13 mm the peripheral arcuate portion having a generally concave lower surface and a generally convex upper surface, the generally concave lower surface being adapted to substantially conform to a generally convex outer surface of at least a portion of a sclera of the patient's eye, and to substantially cover the at least the portion of the sclera of the patient's eye; and one of a stem projecting from a selected position on the peripheral arcuate portion and a lip projecting from at least a portion of an outer periphery of the peripheral arcuate portion;

wherein the corneal cover has a corrective power of substantially 0 diopters; and wherein the corneal cover is made of a hydrophobic material;

preparing the patient's eye for the surgery;

installing the corneal cover on the patient's eye by grasping the one of the stem and the lip with one of a tool and a hand and placing the corneal cover on the patient's eye;

making at least one incision in a portion of the patient's sclera not covered by the peripheral arcuate portion;

inserting at least one surgical instrument into the at least one incision;

observing the surgical site through the central arcuate portion and the patient's cornea; and performing the surgery with the at least one surgical tool.

19. A method as recited in claim 18, wherein performing the surgery with the at least one surgical tool includes performing a vitrectomy.

20. A method as recited in claim 18, wherein installing the corneal cover on the patient's eye includes placing the corneal cover on the patient's eye with a viscoelastic material.

21. A method as recited in claim 18, wherein an interface between the corneal cover and the viscoelastic material defines a tear film, the tear film providing a correction for an astigmatism present in the patient's eye.

22. A method of performing a surgery on a surgical site in a patient's eye, the method comprising:

utilizing a corneal cover, the corneal cover including:
a central arcuate portion having a first radius of curvature, the central arcuate portion having a generally concave lower surface and a generally convex upper surface, the generally concave lower surface being adapted to substantially conform to a generally convex outer surface of a cornea of the patient's eye, and to substantially cover the cornea of the patient's eye; and a peripheral arcuate portion having a second radius of curvature, the peripheral arcuate portion having a generally concave lower surface and a generally convex upper surface, the generally concave lower surface being adapted to substantially conform to a generally convex upper surface of at least a portion of a sclera of the patient's eye, and to substantially cover at the least the portion of the sclera of the patient's eye; wherein the corneal cover has a corrective power of between approximately −4 diopters and +4 diopters; and wherein the corneal cover is made of a hydrophobic material;

preparing the patient's eye for surgery;

making at least one incision in a portion of the patient's sclera;

installing the corneal cover on the patient's eye such that the peripheral arcuate portion of the corneal cover does not cover the at least one incision;

inserting at least one surgical instrument into the at least one incision;

observing the surgical site through the central arcuate portion and the patient's cornea; and performing the surgery with the at least one surgical tool.

23. A method as recited in claim 22, wherein installing the corneal cover on the patient's eye includes grasping one of a stem projecting from a selected position on the peripheral arcuate portion, and a lip projecting from at least a portion of an outer perimeter of the peripheral arcuate portion, with one of a tool and a hand, and placing the corneal cover onto the patient's eye.

24. The method as recited in claim 22, wherein performing the surgery with the at least one surgical tool includes performing a viterectomy.

25. The method as recited in claim 22, wherein the first radius of curvature is between approximately 7 mm and approximately 8.5 mm.

26. The method as recited in claim 22, wherein the second radius of curvature is between approximately 11 mm and approximately 13 mm.

27. The method as recited in claim 22, wherein the corrective power is approximately 0 diopters.

28. The method as recited in claim 22, wherein installing the corneal cover on the patient's eye includes placing the corneal cover on the patient's eye with a viscoelastic material.

29. The method as recited in claim 28, wherein an interface between the corneal cover and the viscoelastic material defines a tear film, the tear film providing a correction for an astigmatism in the patient's eye.

* * * * *